(12) United States Patent
Dao

(10) Patent No.: US 8,609,365 B2
(45) Date of Patent: Dec. 17, 2013

(54) SYSTEM FOR STAINING FUNGI AND PROTOZOA

(75) Inventor: My Lien Dao, St. Petersburg, FL (US)

(73) Assignee: University of South Florida, Tampa, FL (US)

(*) Notice: Subject to any disclaimer, the term of this patent is extended or adjusted under 35 U.S.C. 154(b) by 1508 days.

(21) Appl. No.: 11/535,564

(22) Filed: Sep. 27, 2006

(65) Prior Publication Data

US 2007/0026483 A1 Feb. 1, 2007

Related U.S. Application Data

(62) Division of application No. 10/249,663, filed on Apr. 29, 2003, now Pat. No. 7,157,242.

(60) Provisional application No. 60/319,214, filed on Apr. 29, 2002.

(51) Int. Cl.
*G01N 1/28* (2006.01)

(52) U.S. Cl.
USPC .......................... 435/40.5; 435/34; 435/40.51

(58) Field of Classification Search
None
See application file for complete search history.

(56) References Cited

U.S. PATENT DOCUMENTS 6,344,340 B1 * 2/2002 Dibner et al. ................... 435/29

OTHER PUBLICATIONS

Murray et al., "Manual of Clinical Microbiology", 6th edition ASM Press 1995, p. 37.*
Ge et al., Infection and Immunity, May 2001, p. 3502-3506, vol. 69, No. 5.*
Green et al., Analytical Biochemistry, vol. 56, Issue 1, Nov. 1973, pp. 43-51.*
Al-Jumaily et al., Bios, vol. 47, No. 3 (Oct. 1976), pp. 124-131.*
David et al., The Journal of Biological Chemistry, vol. 273, pp. 32063-32070.*
Green and Pastewka. Simultaneous Differential Staining by a Cationic Carbocyanine Dye of Nucleic Acids, Proteins and Conjugated Proteins, I. Phosphoproteins. The Journal of Histochemistry and Cytochemistry, 1974, vol. 22, No. 8, pp. 767-781. Copyright 1974 by The Histochemical Society, Inc. Printed in U.S.A.
Homer, Denbow and Beighton. Spectrophotometric Method for the Assay of Glycosaminoglycans and Glycosaminoglycan-Depolymerizing Enzymes. Analytical Biochemistry, 1993, No. 214, pp. 435-441. Copyright 1993 by Academic Press, Inc.

* cited by examiner

*Primary Examiner* — Irene Marx
(74) *Attorney, Agent, or Firm* — Robert J. Varkonyl; Molly Sauter; Smith & Hopen, P.A.

(57) ABSTRACT

The present invention provides a method for the staining of fungi and microsporidia for observation with a light microscope based upon the presence of chitin in the composition of these organisms. With the method of the present invention a sample to be analyzed is treated with a solution of Ponceau S and Stains-all dye. The sample is then selectively decolorized and rinsed. The resulting sample is examined with a light microscope, or photographed for a permanent record, to identify the presence of a variety of microorganisms, to include fungi and microsporidia.

1 Claim, 10 Drawing Sheets

FIG. 1
Staining of *Penicillium notatum*
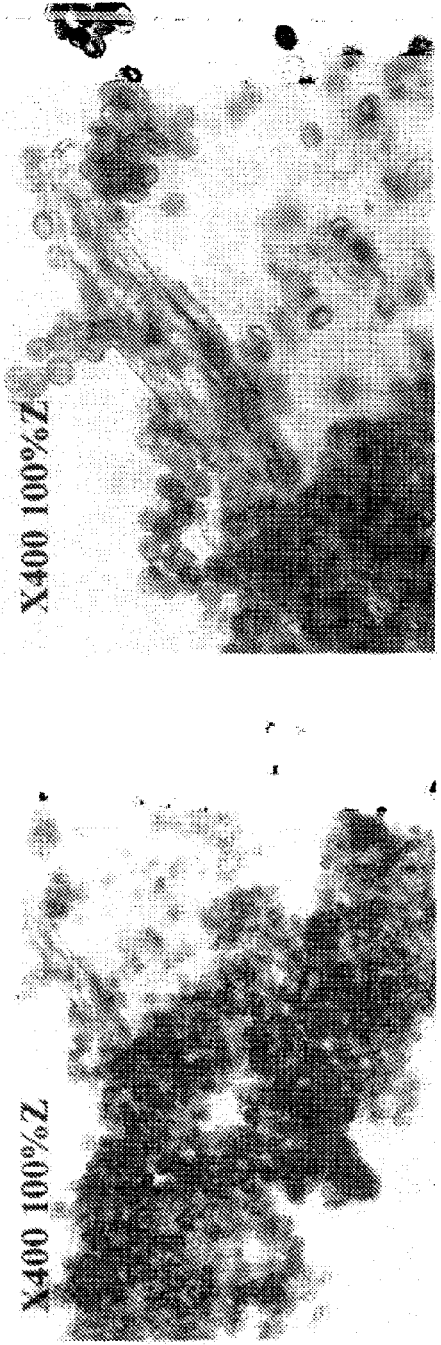
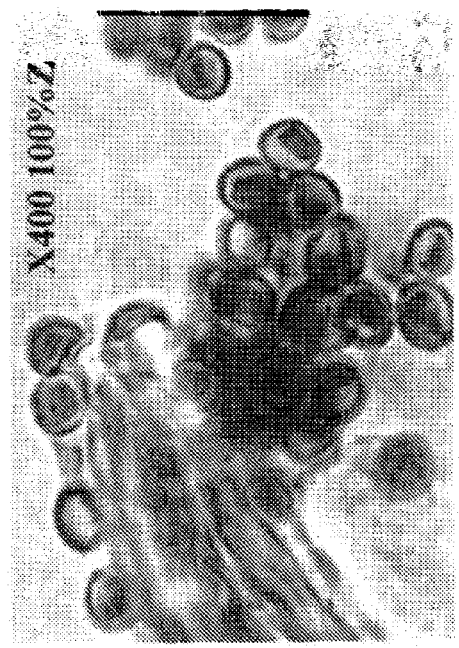

Fig. 2 Staining of *Aspergillus niger*
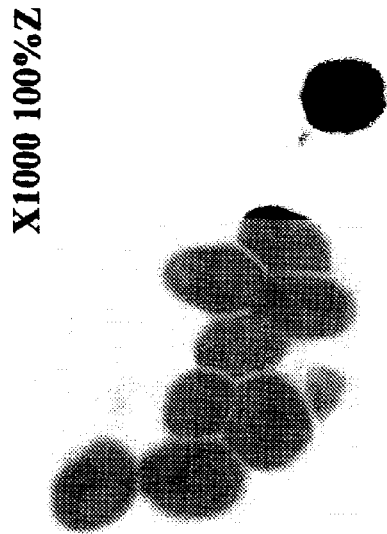
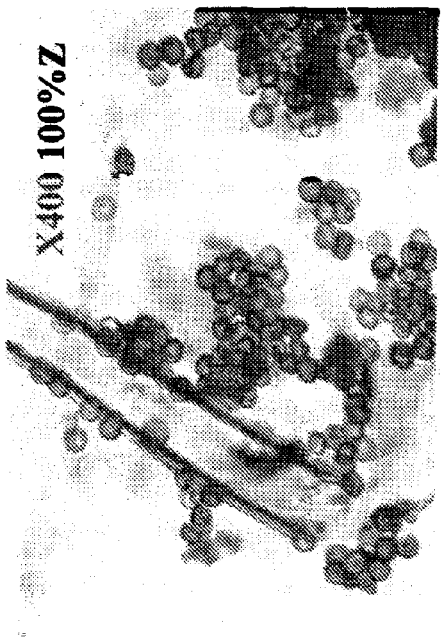
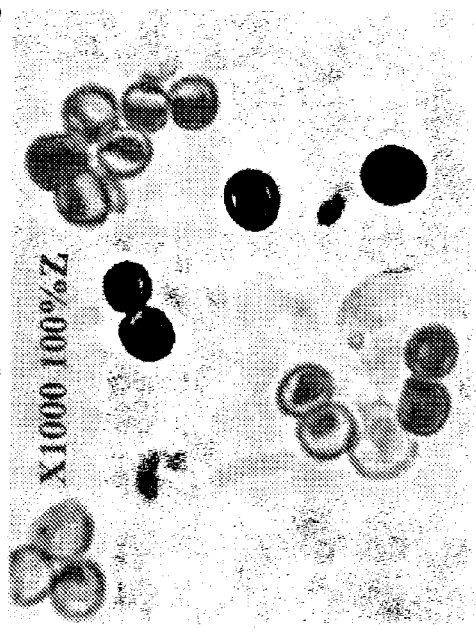

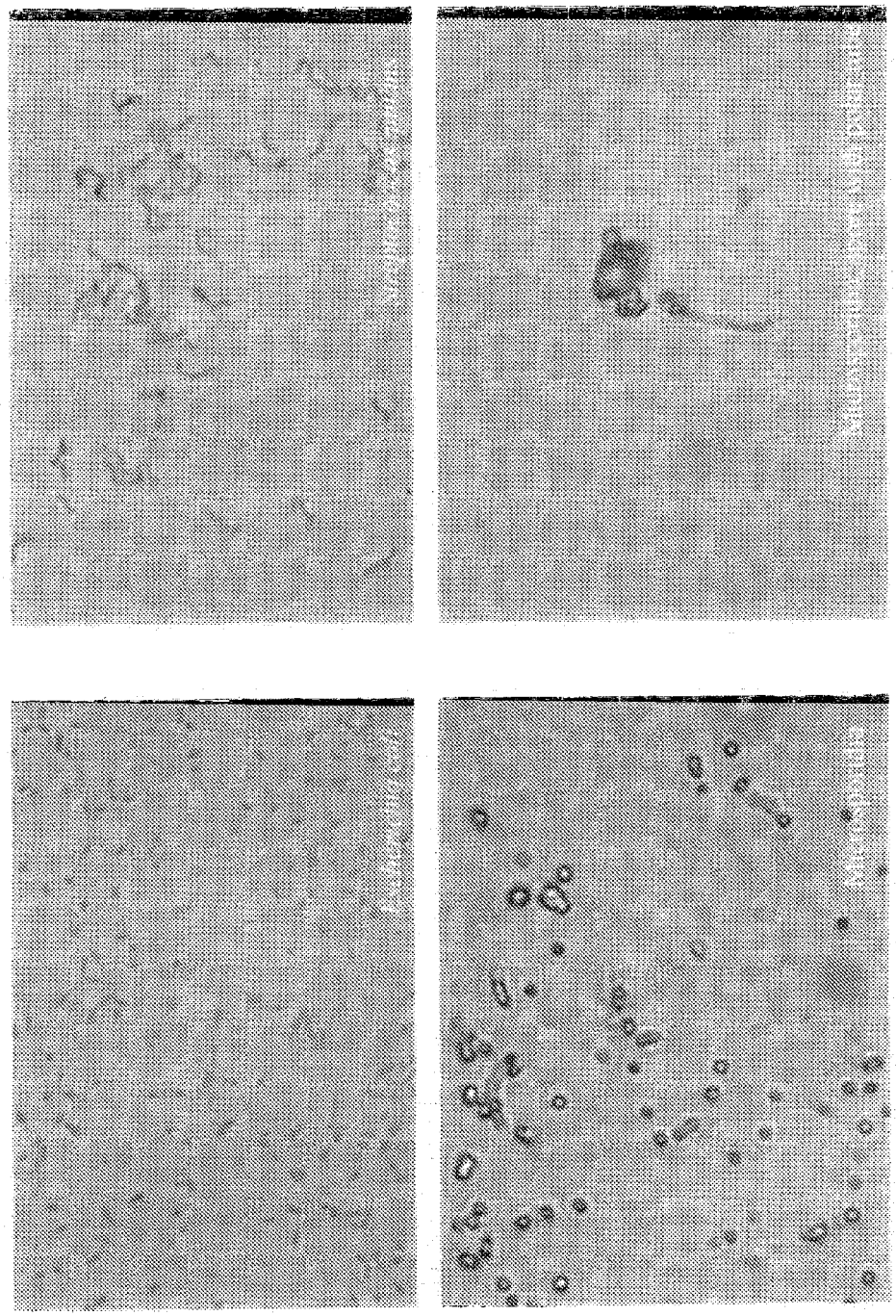
Fig. 3 Staining of Bacteria versus Microsporidia

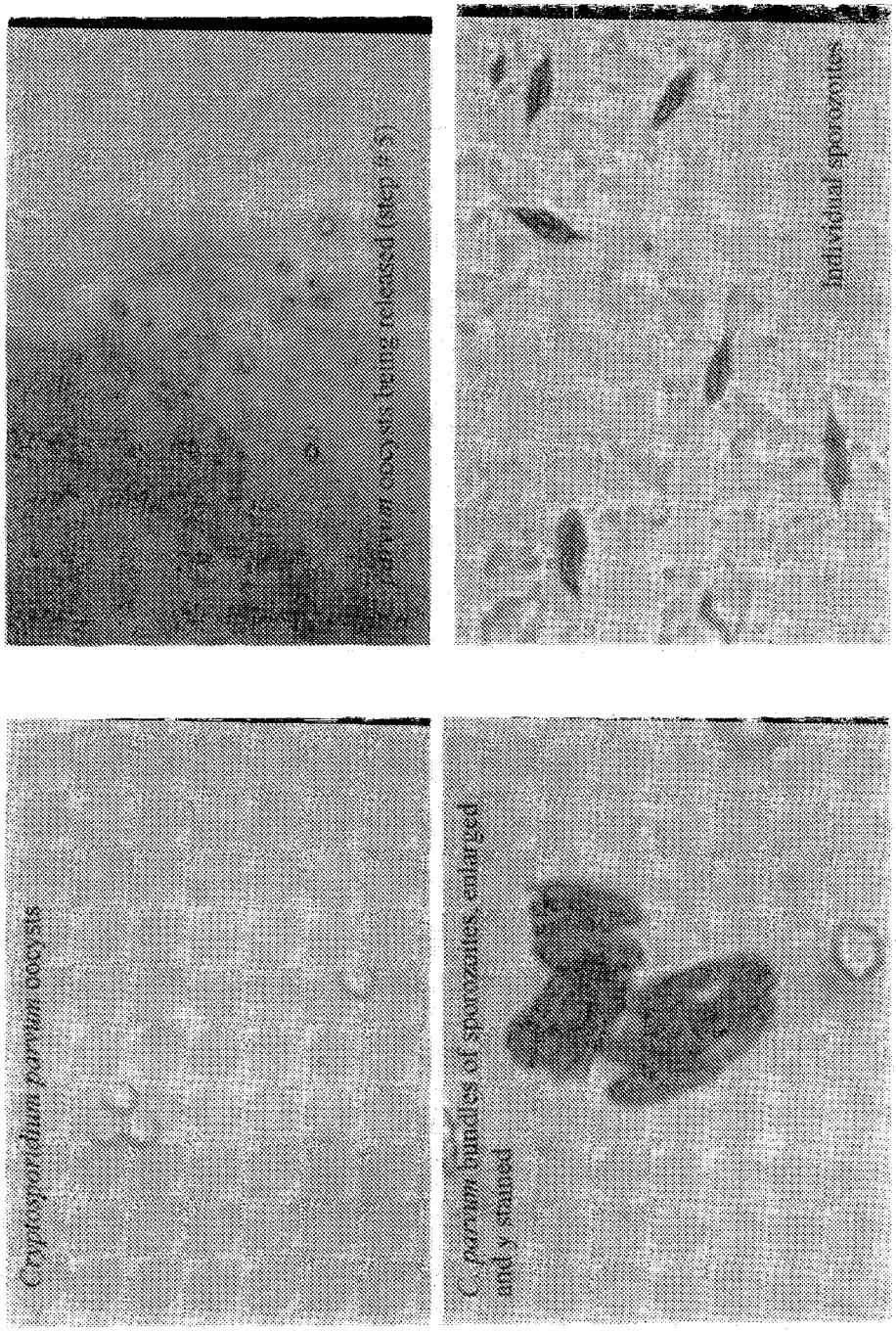

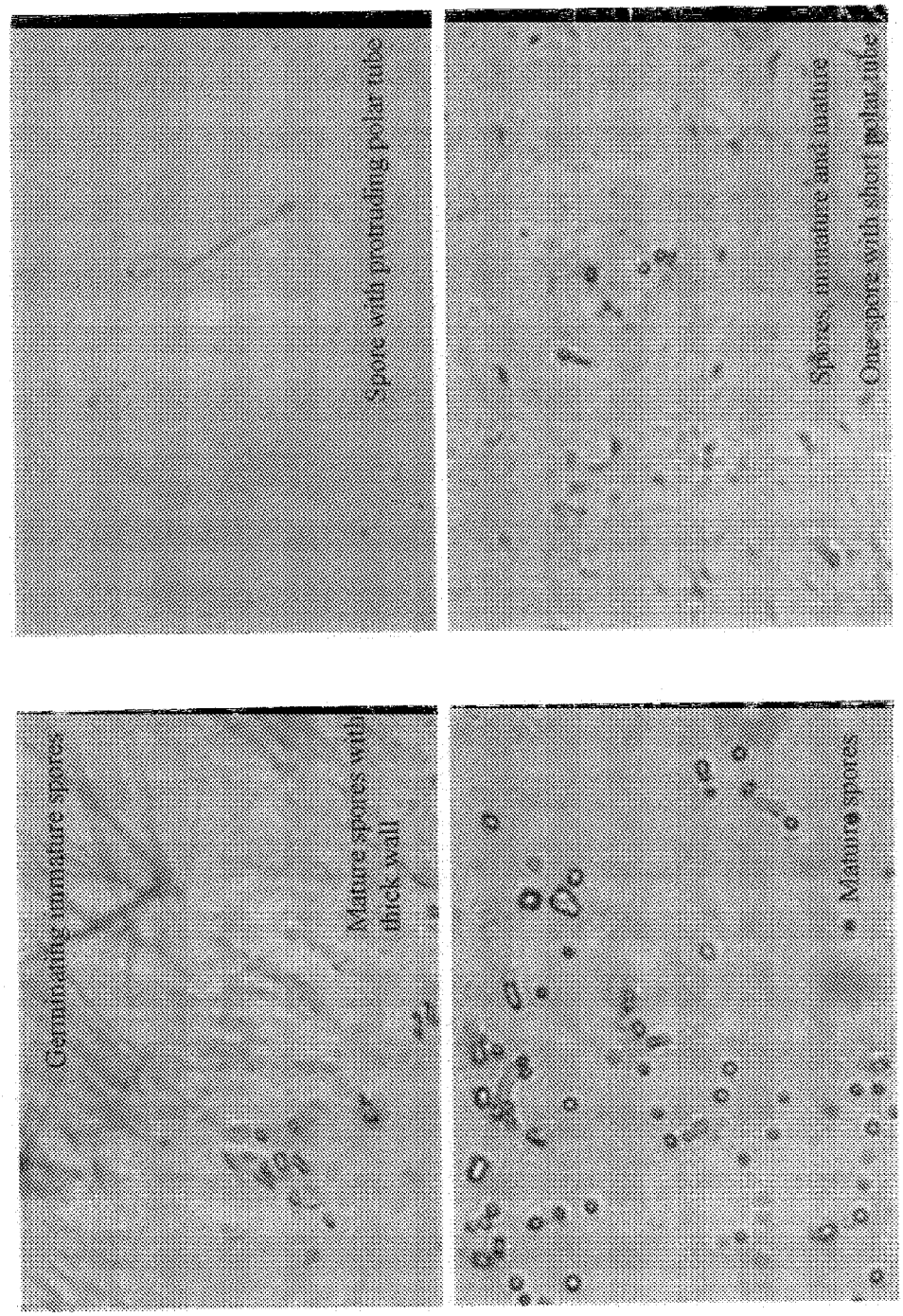
Fig. 5 Staining of Microsporidia

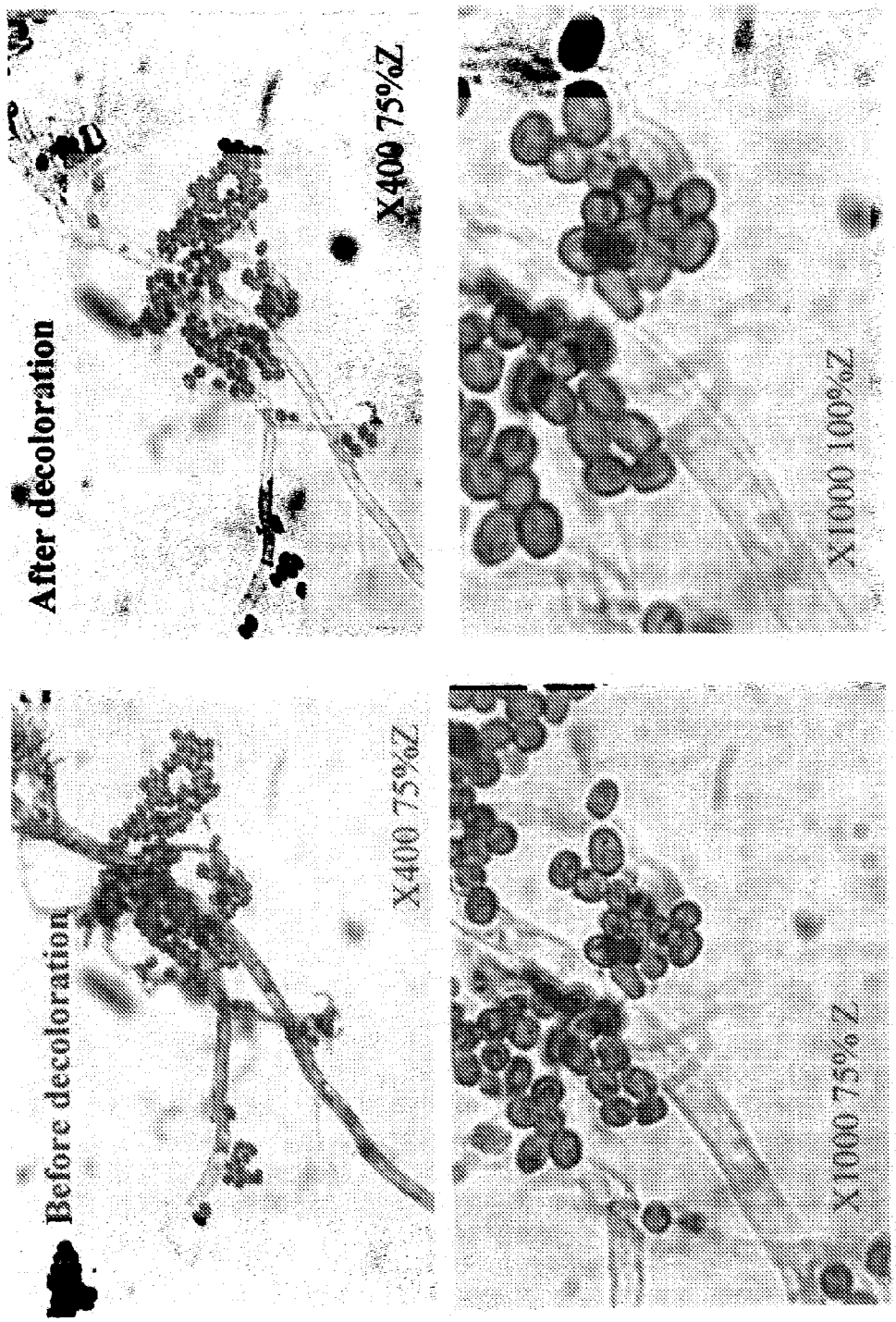
Fig. 6 Staining of *Rhizopus stolonifer*

Fig. 7
Destaining of background
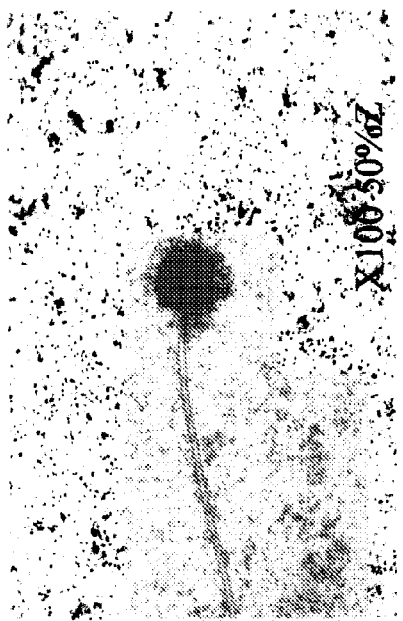
*Aspergillus niger* after destaining
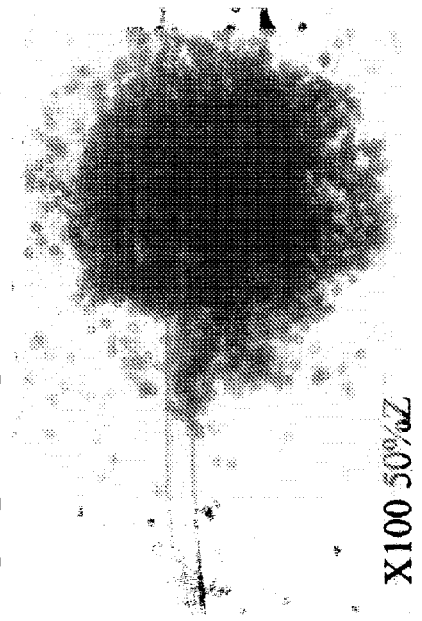
*Aspergillus niger* after destaining
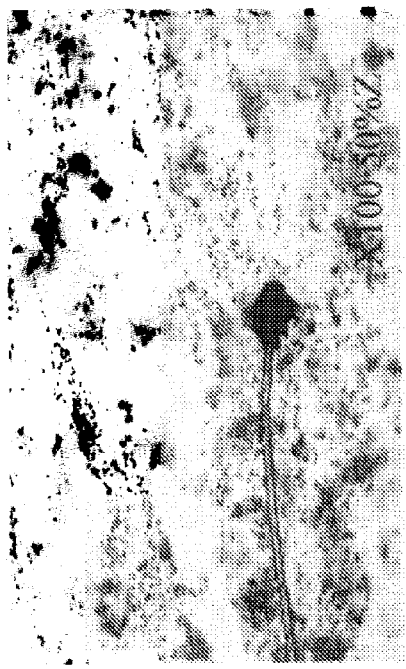
*Aspergillus niger* before destaining
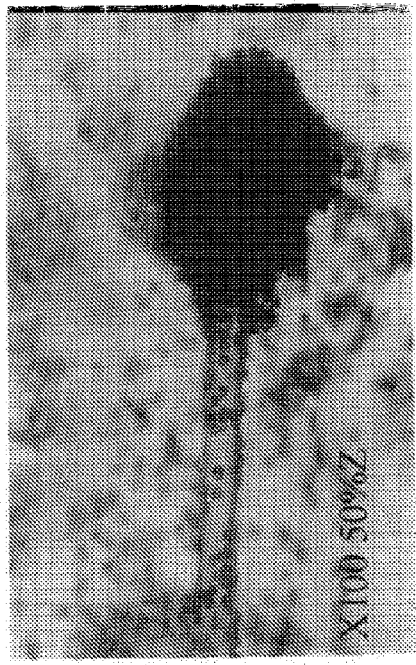
*Aspergillus niger* before destaining Fig. 8 (protocol #1)
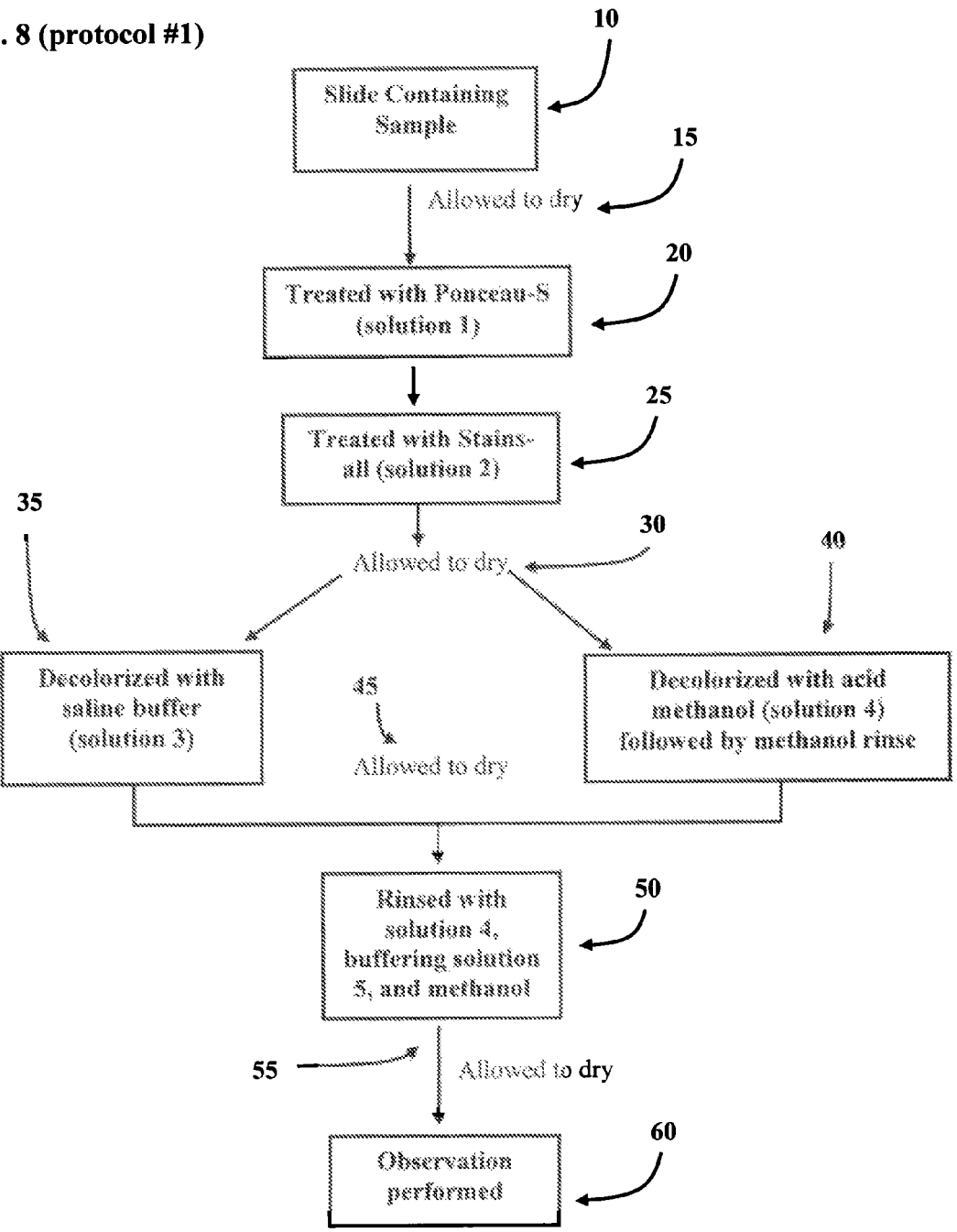

Fig. 9 (Protocol #2)
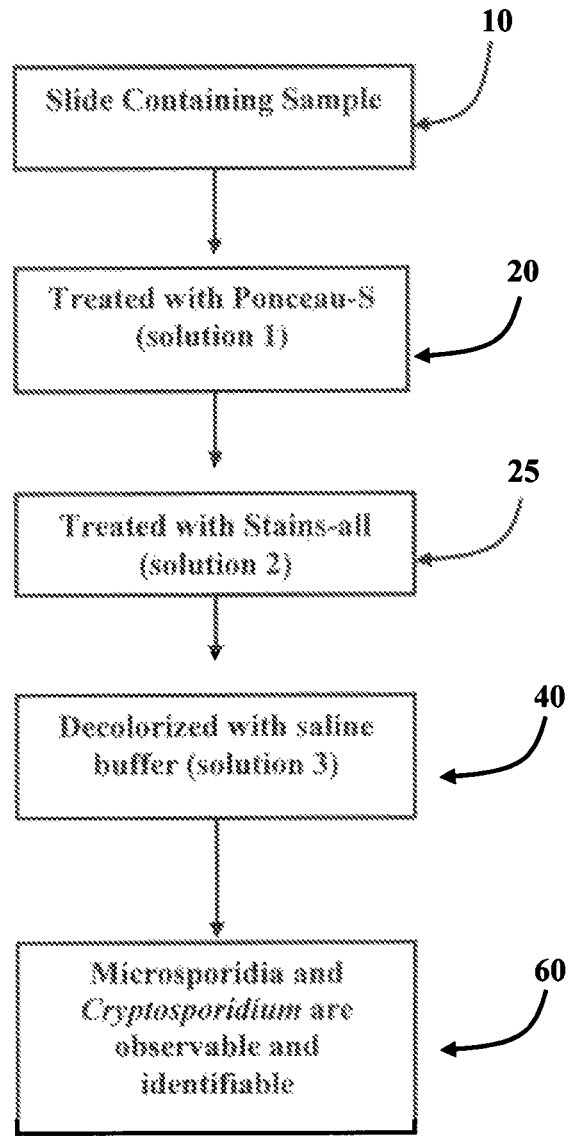

Fig. 10 (Protocol #3)
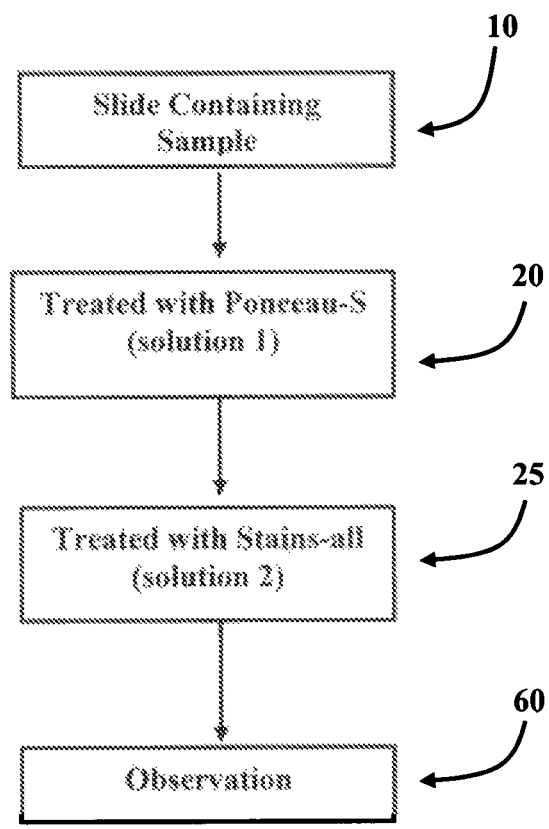

SYSTEM FOR STAINING FUNGI AND PROTOZOA

CROSS REFERENCE TO RELATED APPLICATIONS

This application is a divisional of prior application Ser. No. 10/249,663, entitled "Method for Staining Fungi and Protozoa", filed on Apr. 29, 2003, the contents of which are incorporated herein by reference, which claims the benefit of U.S. Provisional Patent Application 60/319,214, entitled, "Method for Staining Fungi and Protozoa", filed Apr. 29, 2002.

BACKGROUND OF THE INVENTION

This invention is a novel method of staining and detecting protozoa and fungi for observation under a light microscope, and with application to the qualitative and quantitative detection of microsporidia in environmental water samples.

Fungi and microsporidia can be differentiated from other microorganisms based on their chitin content. Current dyes used to stain chitin in fungi and microsporidia are based on fluorescent optical brighteners (Review by Ruchel et al., 2001), requiring a fluorescent microscope for observation. Details are not observable by this method.

A need exists in the art for the identification of the characteristic structures in microsporidian spores, including but not limited to thick spore walls, vacuole, belt-like stripe and sporoplasm, that can be implemented using a light microscope, and recorded using a digital camera.

SUMMARY OF INVENTION

The present invention provides a method for determining the presence or absence of a microorganism in a sample suspected of containing a microorganism. In a preferred embodiment, a sample is provided to be analyzed, the sample is treated with a protein stain, and the sample is then treated with a cationic carbocyanine dye and examined for microorganisms.

In an additional embodiment, the protein stain used to treat the sample is Ponceau S, and preferably is a solution of 0.1% Ponceau S in 5% acetic acid in water.

In an additional embodiment, the cationic carbocyanine dye used to treat the sample is Stains-all, and preferably is a solution of Stains-all in methanol diluted 1:10 in a solution of deionized water, acetic acid, and methanol at 50:10:40.

In an additional embodiment of the present invention, an additional step of selectively decolorizing the sample is included. Selectively decolorizing the sample is facilitated through the application of a decolorizing solution. The decolorizing solution can be a solution of sodium dodecyl sulfate in phosphate buffered saline. Preferably the sodium dodecyl sulfate being 0.25% in phosphate buffered saline. Additionally, the decolorizing solution can be a solution of acid methanol, in a preferred solution of 50:10:40 deionized water, acetic acid, and methanol.

In an additional preferred embodiment of the present invention, an additional step of rinsing the sample prior to examining the sample in included. The rinsing step is facilitated by the application of a solution of acid methanol to the sample and subsequent treatment of the sample with a solution of phosphate buffered saline. Preferably the solution of acid methanol employed in the rinsing step is 50:10:40 deionized water, acetic acid, and methanol and the solution of phosphate buffered saline contains about 0.05% Tween 20.

In a preferred method of the present invention for the determination of the absence or presence of a microorganism in a sample suspected of containing a microorganism, a provided sample is treated with a solution of Ponceau S and Stains-all dye solution. The sample is then selectively decolorized, rinsed and examined for microorganisms.

A kit for detecting the presence of a microorganism is provided by the present invention in which is provided a protein stain and a cationic carbocyanine dye.

In an additional embodiment of the kit, the protein stain is Ponceau S, and preferably a solution of 0.1% Ponceau S in 5% acetic acid in water.

In yet another embodiment of the kit of the present invention, the cationic carbocyanine dye is Stains-all, and preferably a solution of Stains-all in methanol diluted 1:10 in a solution of deionized water, acetic acid, and methanol at 50:10:40.

In an additional embodiment, the kit of the present invention includes a selective decolorizing solution. The decolorizing solution being sodium dodecyl sulfate in phosphate buffered saline, and preferably a solution of 0.25% sodium dodecyl sulfate in phosphate buffered saline. Additionally, the decolorizing solution can be a solution of acid methanol, preferably a solution of 50:10:40 deionized water, acetic acid, and methanol.

In yet another embodiment, the kit of the present invention includes a rinsing solution. The rinsing solution being acid methanol, preferably the solution of acid methanol is 50:10:40 deionized water, acetic acid, and methanol.

In another embodiment, the kit contains phosphate buffered saline solution. Preferably, the phosphate buffered saline solution being 0.05% Tween 20.

BRIEF DESCRIPTION OF THE DRAWINGS

For a fuller understanding of the nature and objects of the invention, reference should be made to the following detailed description, taken in connection with the accompanying drawings, in which:

FIG. 1 are photographic slides of the staining of *Penicillium notatum* using the present invention.

FIG. 2 are photographic slides of the staining of *Aspergillus niger* using the present invention.

FIG. 3 are photographic slides of the staining of *Escherichia coli, streptocoocus mutans*, and microsporidia using the present invention.

FIG. 4 are photographic slides of the staining of *Cryptosporidium* using the present invention.

FIG. 5 are photographic slides of the staining of Microsporidia using the present invention.

FIG. 6 are photographic slides of the staining of *Rhizopus stolonifer* using the present invention.

FIG. 7 are photographic slides of background destaining using the present invention.

FIG. 8 is a flow diagram demonstrating a method identified as Protocol 1 of the present invention.

FIG. 9 is a flow diagram demonstrating a method identified as Protocol 2 of the present invention.

FIG. 10 is a flow diagram demonstrating a method identified as Protocol 3 of the present invention.

DETAILED DESCRIPTION OF THE PREFERRED EMBODIMENT

The method of the present invention is based on three original observations made, including: (1) the strong binding of Ponceau S to chitosan, a derivative of chitin, and presumably other glucoaminoglycans; (2) the stable binding of Stains-all to Ponceau S; (3) the selective removal of dyes from non-chitin containing microorganisms by a PBS solution containing sodium dodecyl sulfate (SDS). Based on this method, convenient staining kits for fungi and microsporidia can be prepared and commercialized for use in research and clinical laboratories, in water analysis, and in food quality control. This method is also amenable to the staining of tissue sections, and automation for the routine analysis of a large number of environmental water samples.

New properties for the dye Stains-all have been observed in the laboratory setting. The dye complexes readily with the dye Ponceau S, causing a shift in the absorption spectrum of both the Ponceau S and the Stains-all dye. Additionally, new properties for the dye Ponceau S have been discovered. This dye is widely used for the staining of proteins in various applications, but it has been heretofore unknown in the prior art that this dye can stain strongly and permanently chitosan, a derivative of chitin. Subsequent to this finding, a protocol was invented to put these properties to use in the staining of fungi, and microsporidia as these organisms are known to contain chitin. Using this protocol, these organisms can be stained and identified, even in a complex mixture.

The preferred protocol of the present invention comprises the following steps (1) preparation of tissue section on slide, or application of the samples to be analyzed onto microscopic slide, followed by drying; (2) sequential addition the dye Ponceau S and the dye Stains-all, followed by drying (3) selective decolorization by addition of SDS to destain non-chitin containing cells or microorganisms followed by drying; (4) sequential rinsing of the slide by acid-methanol, methanol, PBS containing Tween 20, then methanol. The drying step may be performed on a heating block (50° C.) to speed up the process. A light microscope is used for observation.

The staining method of the present invention uses Ponceau S and the Stains-all dyes. Ponceau S is also known as C.I. Acid Red 112, Ponceau Red and Ponceau X Extra. The chemical formula for Ponceau S is 3-hydroxy-4((2-sulfo-4-((-4-sulfophenyl(azo)phenyl-)azo)2,7 naphthalenedisulfonic acid tetrasodium salt. The dye Stains-all, a cationic carbocyanine dye, [7423-31-6] 1-Ethyl-2-[3-(1-ethylnaphtho[1,2-d]thiazolin-2-ylidene)-2-methylpropenyl]naphto[1,2-d]thiazolium bromide, is a sensitive stain for various biochemical components including nucleic acid, hyaluronic acid phosphoproteins and non-phosphorylated proteins, and acid mucopolysaccharides.

Different colors are obtained depending on the nature of the biochemical component. The Stains-all dye interacts with these compounds forming different complexes absorbing at various wavelengths (Kay et al., 1964; Green et al., 1973). Application of the Stains-all dye is limited to the electrophoretic characterization of nucleic acids, proteins (phosphorylated and non-phosphorylated), and substituted polysaccharides in polyacrylamide or composite agarose and polyacrylamide gels (Green et al., 1973; Dalberg et al., 1969; Bader et al., 1972). Stains-all can be used to simultaneously stain nucleic acids, proteins, conjugated proteins and polar lipids (Green, 1975). Although, Stains-all is a sensitive and potentially useful as a differential dye, it has not been used to stain microorganisms. One disadvantage associated with the dye is that it fades rapidly.

Thus, the dye Stains-all used in combination with Ponceau S to stain microsporidia and fungi produces new and unexpected results. By staining with Ponceau S alone, it is not possible to identify these organisms because Ponceau S stains both proteins and polysaccharides in pink or red. As stated above, Stains-all can differentially stain a number of macromolecules, but has not yet been used to stain microorganisms. This dye is also unpopular due to its propensity to fade away. According to the invented protocol, Ponceau S is used first to stain proteins and more strongly chitin before the addition of Stains-all. The latter dye complexes in situ with Ponceau S, enhancing the coloration and providing different tints due to its binding to other components. The resulting effect is a stable coloration, withstanding the selective decolorization step, and allowing the detection and analysis of fungi and microsporidia, even in a complex mixture of microorganisms.

Protocol #1

Protocol #1 as shown in FIG. 8, the preferred staining method as taught by the present invention comprises five solutions: (1) solution of 0.1% Ponceau S in 5% Acetic acid (Ponceau S, Sodium salt is a product of Sigma Chemical Company, St. Louis, Mo.); (2) solution comprising a mixture (1:9, v:v) of 0.2% Stains-all (Stains-all is a product of Acros Organics, NJ) in Methanol (stock solution), which is diluted 1:10 in a solution of acid-methanol (solution 4) before use; (3) solution comprising 0.25% SDS in PBS; (4) solution of Deionized water:Acetic Acid: Methanol (50:10:40); (5) solution of PBS containing 0.05% Tween 20. Preferably, the solutions are supplied in drop-dispensing bottles to simplify the procedure. Additional requirements include Methanol, a heating block set at 50° C., a light microscope, and a digital camera to take micrographs of the slides (Olympus C3030Z or higher).

In an exemplary method, protocol #1, of the present invention, comprises:

APPLICATION OF THE SAMPLE: apply tissue section or aqueous sample containing microorganisms (ex. suspension in PBS) is applied onto a microscopic slide 10, and allowed to dry 15 at room temperature or on a heating block (50° C.);

STAINING: one or more drops of solution 1 20 is added to cover the sample for 10 sec, followed by 2 or more drops of solution 2 25 to cover the sample for 10 sec, pouring off the excess solution and drying 30 at room temperature or on a heating block;

SELECTIVE DECOLORIZATION: 2 or more drops of solution 3 are added to cover the sample 35, and left to stand for approximately three minutes until decolorization of extraneous materials. Then the slide is permitted to air-dry 45 at room temperature or on a heating block (50° C.). Alternatively, an equal volume of acid methanol (solution 4) is added 40 and left in contact for 10 sec, followed by pouring off the excess and rinsing with methanol; Rinsing: The slide is sequentially rinsed 50 with solution 4 added dropwise to cover the sample for 10 sec, followed by methanol, then with solution 5 added dropwise to cover the sample for 10 sec, followed by three rinses with methanol and air-drying 55. Observation is performed on the light microscope 60. Microspodian spores are observable at ×40 based on their darkly stained spore wall, with more characteristics visible at higher magnification.

There are substantial advantages to the present invention. Sensitivity is enhanced. Using protocol #1, differential coloration of fungi, microsporidia, and *Cryptosporidium* is obtained, and detected even in the presence of host cells or other microorganisms, without the need for purification. Non-chitin containing cells such as bacteria (both Gram− and Gram+) and mammalian cells are selectively decolorized by solution 3 in protocol #1. No purification of chitin-containing organisms is needed in the present method, as they are apparent and stand out even in complex mixtures such as septic tank sample, or in presence of bacteria and mammalian cells. Only a light microscope is needed for observation.

Protocol #2

As shown with reference to FIG. 9, it is within the scope of the present invention to modify protocol #1 to establish protocol #2, in which samples are not heated dry before the sequential addition of the dyes at steps 20 and 25, and observation is made upon addition of a drop of solution 3 (SDS) 35 in the middle of the sample. With protocol #2, microsporidia and *Cryptosporidium* can be identified in the same sample 60. The immature microsporidian spores are easily detectable as they are enlarged and elongated while staining in red. *C. parvum* sporozoites, individual or in bundle, stained by protocol #2, are dramatically enlarged and stained in a distinctive red golden brown. Oocysts are released from host cells. Thick walled oocysts do not stain but are apparent, whereas immature oocysts stained in dark red, some of which are enlarged showing stained merozoites or sporozoites in red golden brown. Protocol #2 is allows for the observation of the release of microsporidian spores from parasitophorous vacuoles, followed by a gradual migration of these spores to the periphery of the drop of PBS solution containing SDS, which is accompanied by the germination or elongation of immature spores. Although *Cryptosporidium* does not contain chitin, some staining was observed probably due to the presence of complex carbohydrates such as glucoaminoglycans. Using protocol #2 to stain mammalian cells infected with *C. parvum*, intracellular stages, and thin wall-oocysts are released from the infected mammalian cells and stained in a distinctive red golden brown color at the selective decoloration step. Hence, microsporidia and *Cryptosporidium* can be recognized when present in the same sample when stained by protocol #2.

Protocol #3

In is within the scope of the present invention to modify protocol #1 to establish protocol #3 in which other microorganisms, such as bacteria, are differentially stained. In protocol #3, the selective decoloration step 35 or 40 is omitted. Apparent differences can be observed between different strains of *E. coli*. By omitting the selective decoloration step, as in protocol #3, the use of the dyes Ponceau S and Stains-all can be extended to all other microorganisms for detection based on their difference in size, shape and coloration, properties that can be photographed with a digital camera. For instance, apparent differences are observed with various *Escherichia coli* strains. It is noteworthy that a number of modern biosensors are being developed to analyze microorganisms based on morphological characteristics.

In summary, the invention is useful for the analysis of fungi, and especially useful for the detection of microsporidia and *Cryptosporidium*, in pure sample as well as in complex mixture such as clinical and environmental samples, and perhaps also foodstuffs that do not contain chitin. With the invented method, it is possible to detect microsporidia and *Cryptosporidium* in septic tank samples, and samples of organisms retained on 0.45 um filter from water samples from various sources or sedimented by centrifugation, as well as infected live or formalin-fixed cells and tissues. Additionally, based on the properties mentioned above of the dyes Ponceau S and Stains-all, the present staining method can be modified to stain other microorganisms, which can then be identified based on their size, shape and coloration. Currently, the most specific tests for the identification of microsporidia in water samples are based on genetic method, for example PCR for the amplification of specific genes (Dowd et al., 1999). In this method, the organisms have to be isolated, and their DNA extracted. The sensitivity of the method depends on the efficacy of recovery of the spores from environmental samples by immunomagnetic beads, while DNA isolation from spores is time consuming. This taken with the cost associated with PCR analysis, it is impractical to use genetic tests to routinely and systematically monitor water pollution by microsporidia. The staining method developed in the present invention can be used as a presumptive screening test to identify samples contaminated with microsporidia and/or *C. parvum* for further confirmation by genetic analysis. The entire staining procedure takes less than 30 minutes.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A kit for detecting the presence of a chitin-containing microorganism in a sample suspected of containing the microorganism, comprising in combination:
   a) an aqueous solution of 0.1% 3-hydroxy-4-[2-sulfo-4-(4-sulfophenylazo)phenylazo]-2,7-naphthalenedisulfonic acid tetrasodium salt in 5% acetic acid in water;
   b) a solution of 1-Ethyl-2-[3-(1-ethylnaphtho[1,2-d]thiazolin-2-ylidene)-2-methylpropenyl]naphtho [1,2-d] thiazolium bromide in methanol diluted 1:10 in a solution of acetic acid, methanol and deionized water in a ratio of about 10:40:50, respectively;
   c) a solution of 0.25% sodium dodecyl sulfate in phosphate buffered saline for decolorizing;
   d) a solution of acetic acid, methanol, and deionized water in the ratio of about 10:40:50, respectively for rinsing agent; and
   e) a solution of phosphate buffered saline containing 0.05% Tween 20.

* * * * *